United States Patent [19]

Huc et al.

[11] 4,451,397

[45] May 29, 1984

[54] METHOD OF PREPARING COLLAGEN PRODUCTS

[75] Inventors: Alain R. Huc, Ste-Foy-les-Lyons; Roland L. Allard, Saint-Chamond; Christian L. Chavrier, Caluire, all of France

[73] Assignee: Centre Technique du Cuir, Lyons, France

[21] Appl. No.: 443,759

[22] Filed: Nov. 22, 1982

[30] Foreign Application Priority Data

Nov. 30, 1981 [FR] France ................. 81 22691

[51] Int. Cl.³ .................... C07G 7/00; C08H 1/00; C08H 1/06
[52] U.S. Cl. ..................... 260/123.7; 106/155; 106/157; 128/335.5; 128/DIG. 8; 424/177
[58] Field of Search .............. 260/123.7; 106/155, 106/157; 128/335.5; 424/177

[56] References Cited

U.S. PATENT DOCUMENTS

| | | | |
|---|---|---|---|
| 3,527,225 | 9/1970 | Smith | 260/123.7 X |
| 4,060,081 | 11/1977 | Yannas et al. | 128/156 |
| 4,140,537 | 2/1979 | Luck et al. | 260/123.7 |
| 4,280,954 | 7/1981 | Yannas et al. | 260/123.7 |
| 4,294,753 | 10/1981 | Urist | 260/123.7 |
| 4,350,629 | 9/1982 | Yannas et al. | 260/123.7 |
| 4,378,017 | 3/1983 | Kosugi et al. | 260/123.7 X |

FOREIGN PATENT DOCUMENTS 7621654 7/1976 France .
2362632 3/1978 France .
1190879 10/1968 United Kingdom .

OTHER PUBLICATIONS

Chem. Abstracts, vol. 92, 1980, 142023h, Cundall et al.
Chem. Abstracts, vol. 91, 1979, 181406j, Silver et al.
Collagen-Glycosaminoglycan Interactions, Jackson, D. S., and Bentley, J. P., pp. 189–214.
The Properties and Functions of Connective Tissue Polysaccharides, Laurent, T. C., pp. 27–33, Struct. Fibrous Biopolym., Colston Paper 26.
Polysaccharide-Collagen Interactions, Obrink, B., pp. 81–92, Struct. Fibrous Biopolym, Colston Pap. 26.
Stability of Collagens from Articular Cartilage and from the Heart Valves of Pigs, Study of Collagen–Proteoglycan Interactions, Huc, A. et al, Proteids of the Biological Fluids, 22nd Colloquium, Pergamon Press, 1975.
Collagen and Proteoglycan Interactions in Bovine Articular Cartilage, Herbage, D. et al, Biochimica et Biophysica Acta., 336, (1974), pp. 108–116.

Primary Examiner—Howard E. Schain
Attorney, Agent, or Firm—Karl F. Ross; Herbert Dubno

[57] ABSTRACT

New and highly stable preparations containing collagen in association with mucopolysaccharides are obtained by combining a homogeneous gel or solution of crosslinked or decrosslinked collagen, and a solution of CSA or CSC, and bringing the pH to 7.

6 Claims, No Drawings

METHOD OF PREPARING COLLAGEN PRODUCTS

FIELD OF THE INVENTION

The present invention relates to a method of preparing collagen products and, more particularly, to a process for producing new forms of collagen in a pure or dereticulated (decrosslinked) form, with its helicoidal structure preserved and in association with mucopolysaccharides. The invention thus relates to the production of such new collagen products and also to the use thereof in cosmetology, pharmacology, analytical, therapeutic applications and the like.

BACKGROUND OF THE INVENTION

Connective tissues and particularly the skin are constituted principally by collagen.

Collagen is a fibrous protein comprising most of the white fiber in the connective tissues of animals and man, especially in the skin, muscles and tendons. It is rich in proline and hydroxyproline. The molecule is analogous to a three-strand rope in which each strand is a polypeptide chain. It has a molecular weight of about 100,000.

This protein is responsible for most of the skin structure.

In the course of aging, the collagen crosslinks, i.e. reticulates, a process which has been referred to as polymerization of the polypeptide chains, and the skin wrinkles. The crosslinking process is accompanied by a reduction in elasticity as well. This action, while preserving the helicoidal configuration of the polypeptide chains, accounts in large measure for the aging of the skin.

The skin also contains two other types of macromolecules which are of significance, namely, the elastins and the proteoglycans. While the elastins contribute to the elasticity of connective tissue, they do not react materially with collagen. The proteoglycans, however, have an effect upon the properties of the skin at least in part because of their interactions with collagen. The proteoglycans are macromolecules constituted of hyaluronic acid and protein substances with glycosaminoglycans.

Others have also studied the mechanism of this interaction:

T. C. LAURENT, COLSTEN PAP, 26, Struct. Fibrous Biopolym., 1975, 27-33; A. HUC, P. MANNSCHOTT, D. HERBAGE et M. WEISS, 1975, Protides of Biological Fluids, 22nd colloquium (H. PEETERS ed.), p. 91, Pergamon Press, Oxford and New York; D. HERBAGE, J. M. LUCAS, A. HUC, Biochim. Biophys. Acta, 336, 1974, 108-116.

Certain authors have shown the influence of this interaction on the mechanical properties of the tissues-JACKSON and BENTLEY (1968) in "Treatise on Collagen" (GOULD B. S. ed.), vol. 2A, p. 189, Academic Press, New York.

Thus it appears that the glycosaminoglycans have a number of charged groups and are surrounded by a large number of water molecules which confers to the tissues containing same at least part of their suppleness and a moisturizing effect. The action of the glycosaminoglycans on the skin can be summarized in three points:

protection of the native structure of the collagen;

influence on the mechanical properties of the tissue tending to maintain the suppleness thereof; and hydration or moisturization of the skin.

Thus the association of the glycosaminoglycans with collagen are of interest for a variety of applications.

It is also known that collagen is partially soluble in aqueous solutions by the action of organic or mineral reagents. However, the solubility is poor and, for example, it is only possible to solubilize a relative small fraction of the collagen in most acid media.

Numerous techniques have been proposed not only to permit extraction of the soluble fraction of the collagen but also to increase the solubility of that portion which is generally considered insoluble. These methods have generally been based upon a pretreatment of the starting material with acid or other chemical agents or enzymes which are more or less specific.

Other techniques utilize, for example, the action of heat in an aqueous medium but can result in denaturation of the collagen to gelatin, a hydrolysis of the collagen and/or a breaking of the crosslinking bonds of the molecule and hence destruction of the helicoidal configuration thereof.

As a rule, the fractions of the collagen, which are soluble in aqueous media, have pH values less than or equal to 4. In certain cases this acidity can present significant disadvantages with respect to the use of soluble collagen in analytical conditions where these pH values are lower than physiological pH. Other disadvantages arise from use of the low pH fraction in topical or like applications for treatment where the physiological pH is higher as is the case in cosmetic and dermatological applications and topical therapy.

It is also known that collagen has an isoelectric point close to physiological pH and that the neutralization of the soluble fraction of collagen will generally result in precipitation. So only an extremely small fraction appears to remain soluble after such neutralization.

Furthermore, when mucopolysaccharides (glycosaminoglycans) such as chondroitin-4-sulfate (CSA) or chondroitin-6-sulfate (CSC) acids are added in large proportions to an aqueous solution of the native collagen, the collagenous protein precipitates as a result of the physical interaction between the two compounds.

It has also been proposed to associate collagen with mucopolysaccharides for various collagen treatments. For example in French Pat. No. 2,362,632, it is proposed to incorporate into a serum a certain quantity of glycosaminoglycan and of collagen, together with agents facilitating the lipolysis of adipose tissue. In this patent, proportions of the active proponents are given in dry form and there is no implication that it is possible to achieve a clear solution or a homogeneous gel.

Japanese patent KOKAI No. 79-52733 (Chemical Abstracts, vol. 91, 1977, p. 332-abstract 216,6770) also deals with mixtures of this type but without any indication that the compositions obtained are homogeneous or any indication even that a homogeneous quality is important since the large proportion of excipient provided completely buries the active composition in a cream in which in fact the precipitate is dispersed.

Cundall R. B. et al (Int. J. Biol. Macramol. 1979, 1 (5) 215-22) (Chem. Abstr. vol. 92, 1980, p. 179, ref. 142023h) have studied the electrostatic interactions brought about between the polyanions and the proteins, most specifically in the case of complexes formed at a pH of 3 between collagen and certain mucopolysaccharides and have determined that these complexes disassociate when the pH is raised from 3 to 9.

In the J. Biomed. Mater. Res. 1979, 13 (5) 702-16 (Chem. Abstr., vol. 91, 1979, p. 290, ref. 181406j), a study is described of the compatibility in blood in vitro of collagen/mucopolysaccharide systems, which are significantly more compatible with the blood than pure collagen. This reference points out that collagen is precipitated by CSC at a low pH.

In U.S. Pat. No. 3,527,225 (Example 1) an effort to obtain a solution of a mixture of collagen and chondroitin sulfuric acid is described. However, under the conditions set forth, it is not possible to operate with a mucopolysaccharide concentration greater than 3% with respect to the concentration of collagen.

French Pat. No. 2,332,863 describes an attempt to fabricate a synthetic skin by providing a multi-layer membrane of a composition produced by the intimate contact of collagen and a mucopolysaccharide followed by a crosslinking thereof. It should be apparent that the coprecipitation which results in the product in an aqueous medium precludes obtaining clear solutions or homogeneous gels thereof.

OBJECTS OF THE INVENTION

It is the principal object of the present invention to provide a process for producing a clear solution or homogeneous gel composition of the glycosaminoglycan mucopolysaccharides in its active or decrosslinked form while preserving its helicoidal structure and hence the essential physical and chemical properties of the collagen.

Another object of the invention is to provide improved compositions for cosmetic, dermatological, analytical and therapeutic purposes which avoids the problems hitherto encountered with earlier systems.

DESCRIPTION OF THE INVENTION

According to the invention, these objects are attained with a process for producing compositions of collagen and mucopolysaccharides which comprises treating the collagen in its natural or decrosslinked state in the form of a homogeneous suspension or a solution, with a solution of a glycoasminoglycan, and thereafter bringing the pH of the mixture to 7.

According to one embodiment of the invention, the crosslinking bonds of the collagen are first destroyed, i.e. the collagen is decrosslinked by prolonged contact of collagenous tissue with a stronger alkali solution (aqueous soda or preferably sodium hydroxide) at a pH preferably of 14, the composition then resulting from the treatment of the collagen with glycosaminoglycan being obtained in the form of a clear solution.

In another embodiment of the invention, the native collagen is used in the form of a gel obtained from dehydrated collagenous fibers and the association product resulting from the treatment of the collagen with the glycosaminoglycan is in the form of a homogeneous gel.

In the mixture, the collagen concentration is preferably about twice the concentration of the glycosaminoglycan.

The mixture of the present invention can be used in numerous applications and in compositions appropriate to these applications, such as solutions, powders, sponges (bibulous supports which can be impregnated in turn with solutions and suspensions or can form a synthetic dermatological or osteological tissue), films, tubes, bristles or fibers, etc. The compositions can be used in cosmetology, pharmaceutics, veterinary and other therapeutic applications, including periodontology and bone surgery. The product is especially effective for use as homostatic or tissue dressing, and can be used in clinical applications, as supports for active molecules such as enzymes, i.e. as a substrate carrier in various forms of analysis.

SPECIFIC EXAMPLES

EXAMPLE 1

Preparation of a composition according to the invention in the form of a clear solution of decrosslinked collagen and CSA (a) Preparation of chondroitin-4-sulfate acid from the nasal septa of cattle The fresh nasal septa are thoroughly washed in a solution of 9 parts of sodium chloride with 1,000 parts of water. They are then shredded and ground. The ground product in an amount of 1 kg per liter is treated with an 0.5 N solution of potash. After agitation, the mixture is permitted to stand at ambient temperature for 24 hours.

Thereafter the supernatant liquid is separated from the insoluble material by centrifugation at 30,000 g over a period of 50 minutes. Pure acetic acid is added to the supernatant to neutralize it to pH 7 and the solution is then concentrated to one fifth of its original value, i.e. 5 times, by evaporation in vacuum. The concentrate is combined with a three times greater volume of ethanol to precipitate out the CSA. The precipitate recovered by decantation is dissolved in water which has previously been subjected to ion exchange for purification and the chondroitin-4-sulfate acid is recovered by lyophilization of this solution.

(b) Preparation of the decrosslinked collagen

Veal hide, recovered from freshly slaughtered animals, is scrubbed in tap water for one hour in a filling tub.

The hair and subcutaneous tissue are separated from the derma by a rotating band splitter. The dermal tissue thus recovered is chopped and ground.

The ground product is then washed in three successive baths with a phosphate buffer of pH 7.8. Between each washing the ground product is separated from the solution by continuous centrifugation at 4000 rpm. The residue is then rinsed in two successive baths of deionized water and the liquid is separated from the solids in the same manner as for the washing. These initial treatments serve to eliminate the noncollagenous substances.

The tissue is then placed in a flask containing an aqueous sodium hydroxide solution at pH 14. After agitation of about half an hour, the mixture is permitted to stand for eight days. The mixture is then acidified with hydrochloric acid to a pH of 2. To the mixture thus obtained, sodium chloride is added to a concentration of 10%. The collagen precipitates and is dialysed against sterile deionized water.

(c) Preparation of the clear solution according to the invention

The dialysed collagen gel of a concentration of 1.2% is diluted at a ratio of two parts to one with a solution containing 0.6% of the chondroitin-4-sulfate prepared as in (a), 0.4% of a commercial preservative maketed under the name of Phenonip being added. A 0.1 N solution of sodium hydroxide is added to the mixture until the pH is raised to 7. At this point the clear solution has a collagen concentration of 0.6% and glycosaminoglycan concentration of 0.4%.

The solution is readily incorporated into cosmetic creams, for example, for applications to the skin.

It has been found that this solution can also improve the skin tone when incorporated in face masks used in cosmetology and bone surgery, as an enzyme support in analysis and in synthetic skin tissue or the like.

In other cases, a homogeneous gel structure is preferred so that the product can be transformed into sponge or the like as described in Example 2.

EXAMPLE 2

Preparation of a homogeneous gel according to the invention (a) Preparation of CSC (chondroitin-6-sulfate acid)

The chondroitin-6-sulfate acid can be prepared from shark fins following the process described in Example 1, part (a).

(b) Preparation of a homogeneous suspension of collagen

A paste of collagen from animal skin is formed by grinding and kneading the product with chlorinated organic acids as described in French Pat. No. 1,568,829. This paste is diluted with water to obtain 1% concentration of collagen in the product. The protein in this solution is precipitated by the addition of 10% sodium chloride thereto. The resulting fibers are separated from the supernatant by continuous centrifugation at 4000 rpm. They are then dehydrated by treating with three successive baths of acetone and then dripping off the acetone by heating to 30° C. in a ventilated steam room. The fibers are introduced into deionized water in an amount of 2 g per liter. After agitation for one hour, the gel is obtained.

(c) Preparation of a homogeneous gel of the composition according to the invention To the gel obtained by step (b) above, a volume equal to a solution of 1 g per liter of the CSC acid prepared in step (a) is added.

The gel has a tendency to break down and a dispersion is thus obtained. A solution of 0.1 N of sodium hydroxide is added with agitation to the mixture until the pH is raised to 7. Thus the dispersion is transformed anew into a homogeneous gel.

This gel can be formed into a sponge by lyophilizing it in the form of a layer having a thickness of 10 mm or less.

This sponge has a composition approximating that of bony support tissue and can be used as a filler or prosthetic replacement for bone tissue in bony cavities and to promote rehabilitation of these cavities by the osteocytes. Thus the product is extremely useful in peridontology and bone surgery.

Actually the invention is not limited to the specific examples given nor the applications therein which have been specifically described and can be utilized in all of the many ways described more broadly herein to the extent that such applications fall within the spirit and scope of the appended claims.

We claim:

1. A method of preparing a collagen mucopolysaccharide composition in the form of a clear solution which comprises the steps of:
   (a) contacting ground collagenous material with an alkali solution having a pH of 14 for a prolonged time period to form a collagenous mixture;
   (b) acidifying the collagenous mixture formed during step (a) to a pH of 2 to form decrosslinked collagen in the form of a solution or gel; and
   (c) combining the decrosslinked collagen in the form of a solution or gel with a solution of a glycosaminoglycan, and then bringing the pH of the combined solutions to 7 by addition of alkali, thereby producing the desired product.

2. The method defined in claim 1, step (c), wherein the concentration of collagen is about twice the concentration of the glycosaminoglycan.

3. A method of preparing a collagen mucopolysaccharide composition in the form of a homogeneous gel which comprises the steps of:
   (a) obtaining crosslinked natural collagen in the form of a gel from dehydrated collagen fibers; and
   (b) combining the crosslinked natural collagen in the form of a gel with a solution of a glycosaminoglycan, and then bringing the pH of the combined solutions to 7 by the addition of alkali, thereby producing the desired product.

4. The method defined in claim 3, step (b), wherein the concentration of collagen is about twice the concentration of the glycosaminoglycan.

5. The method defined in claim 3, further comprising the step of:
   (c) lyophilizing the collagen mucopolysaccharide composition in the form of a gel to form a layer having a thickness of 10 mm or less, thereby forming a sponge.

6. A method of promoting the growth of bone which comprises the step of applying to a site where osteocytes are active a sponge formed according to claim 5.

* * * * *